(12) United States Patent
Gerhardt et al.

(10) Patent No.: US 7,332,087 B2
(45) Date of Patent: Feb. 19, 2008

(54) FLOW SENSING APPARATUS USED TO MONITOR/PROVIDE FEEDBACK TO A SPLIT FLOW PUMPING SYSTEM

(75) Inventors: Geoff C. Gerhardt, Millbury, MA (US); Keith Fadgen, Hope Valley, RI (US)

(73) Assignee: Waters Investments Limited, New Castle, DE (US)

( * ) Notice: Subject to any disclaimer, the term of this patent is extended or adjusted under 35 U.S.C. 154(b) by 478 days.

(21) Appl. No.: 10/723,973

(22) Filed: Nov. 26, 2003

(65) Prior Publication Data

US 2005/0109699 A1    May 26, 2005

(51) Int. Cl.
*B01D 15/08* (2006.01)

(52) U.S. Cl. ............... 210/656; 210/659; 210/101; 210/198.2; 436/161

(58) Field of Classification Search .......... 210/656, 210/659, 101, 198.2; 422/70; 436/161
See application file for complete search history.

(56) References Cited

U.S. PATENT DOCUMENTS

| | | | |
|---|---|---|---|
| 3,917,531 A | 11/1975 | Magnussen | 210/31 |
| 4,003,243 A | 1/1977 | Blu | 73/61.1 |
| 4,174,772 A | 11/1979 | Neuss | 435/32 |
| 4,840,730 A | 6/1989 | Saxena | 210/198.2 |
| 5,004,538 A | 4/1991 | Apfel | 210/198.2 |
| 5,035,138 A | 7/1991 | Abdel-Rahman | 73/204.12 |
| 5,234,586 A | 8/1993 | Afeyan | 210/198.2 |
| 5,306,426 A | 4/1994 | Afeyan | 210/198.2 |
| 5,346,622 A | 9/1994 | Klee | 210/659 |
| 5,491,096 A | 2/1996 | Sportsman | 436/518 |
| 5,614,089 A | 3/1997 | Allington | 210/198.2 |
| 5,630,706 A | 5/1997 | Yang | 417/3 |
| 5,637,790 A | 6/1997 | de Corral | 73/54.06 |
| 5,938,932 A | 8/1999 | Connelly | 210/659 |
| 6,106,710 A | 8/2000 | Fischer | 210/659 |
| 6,386,050 B1 | 5/2002 | Yin | 73/861.95 |
| 6,402,946 B1 * | 6/2002 | Spraul et al. | 210/198.2 |
| 6,460,420 B1 | 10/2002 | Paul | 73/861.52 |
| 6,627,075 B1 * | 9/2003 | Weissgerber et al. | 210/198.2 |
| 2002/0146349 A1 | 10/2002 | Gygi et al. | 422/70 |
| 2002/0158022 A1 | 10/2002 | Huang | 210/656 |

FOREIGN PATENT DOCUMENTS

| | | |
|---|---|---|
| DE | 199 14 358 A1 | 10/2000 |
| DE | 199 14 358 C2 | 5/2001 |
| EP | 1 248 096 B1 | 9/2002 |
| JP | 4-115158 | 4/1992 |

* cited by examiner

*Primary Examiner*—Ernest G. Therkorn
(74) *Attorney, Agent, or Firm*—Anthony J. Janiuk; Jamie H. Rose; Brian Michaelis

(57) ABSTRACT

A method and apparatus for monitoring and controlling the nano-scale flow rate of fluid in the operating flow path of a HPLC system without relying on a nano-scale sensor in the operating flow path. A main flow sensor is disposed in the main flow path between the pump and a flow-divider. A waste flow sensor is disposed in the waste flow path downstream of the splitter. The output signal of the waste flow sensor is subtracted from the output signal of the main flow sensor in a difference circuit. The difference signal is divided by the output signal from the main flow sensor in a divider circuit. The output of the divider circuit represents an empirical split ratio of the flow-divider and is independent of media composition.

5 Claims, 9 Drawing Sheets

FLOW SENSING APPARATUS USED TO MONITOR/PROVIDE FEEDBACK TO A SPLIT FLOW PUMPING SYSTEM

FIELD OF THE INVENTION

The present invention relates to a flow sensing method and apparatus and more particularly to a flow sensing method and apparatus used to monitor and provide feedback to a split-flow pumping system which enables the delivery of stable flow to a nano-scale chromatographic system using a micro-scale or normal scale chromatographic pump.

BACKGROUND OF THE INVENTION

Traditional plunger displacement pumping systems have been successful in delivering stable, accurate flows in the normal-scale and micro-scale high performance liquid chromatography (HPLC) regimes. While normal-scale HPLC is performed with mobile phase flow rates of about 0.1-5.0 mL/min and micro-scale HPLC is performed with mobile phase flow rates of about 1-100 μL/min, nano-scale HPLC requires mobile phase flow rates in the 50-500 nL/min range. Plunger displacement pumping systems can not deliver nano-scale HPLC flow rates with reliability and accuracy.

One method for providing nano-scale flow rates in an HPLC system is to use a flow-divider which directs a majority of flow from the pump to a waste stream and a small portion of the pump output to the HPLC working stream (i.e., to the liquid chromatography column). A split restrictor in the waste stream and/or the working stream controls the split ratio of the system. Normal-scale or micro-scale HPLC pumps can be used in split flow mode to produce nano-scale HPLC flow rates in the working stream.

In order to operate an HPLC system in split-flow mode the user must calculate the split ratio of the system. To calculate the split ratio, the user must know the permeabilities of both the split restrictor and the chromatographic system (i.e. the packed column). These permeabilities are used to calculate the flow rate that must be supplied by the normal-scale or micro-scale HPLC pump to produce the desired flow through the chromatographic system. Although it is possible to calculate split restrictor dimensions that should provide a desired split ratio, changes in permeability of either the split restrictor or chromatographic column over time cause unpredictable split ratio variations. Such variations result in unacceptable flow variations through the chromatographic column.

One possible solution to the problem of changing split ratios is to monitor the flow to the chromatographic column with an appropriate flow sensor. Fluid flow rates can be determined by measuring the pressure of a liquid flowing through a restrictor. Assuming a constant viscosity, the back pressure of liquid flowing through a restrictor will scale linearly with the flow rate of the liquid. The flow rate is measured by placing a pressure transducer before and after a restrictor inline with the flow. Signals from the pressure transducers are electronically subtracted and amplified to achieve a high degree of common-mode noise rejection.

The permeability of the restrictor is chosen so that it provides sufficient back pressure to produce a measurable pressure difference signal (ΔP) in the flow ranges of interest but does not produce a significant back pressure for the pump. For example, a 10 cm long, 25 μm inside diameter capillary will provide a back pressure of approximately 100 pounds per square inch (psi) for water flowing at 5 μL/min. This permeability is sufficient for providing a flow measurement while not inducing much fluidic load on the pump.

However, pressure measuring flow sensors must be calibrated to compensate for the different viscosity of each fluid being measured. This creates a great disadvantage in liquid chromatography applications wherein fluid composition varies dramatically over the course of a chromatography run.

Another method that can be used to sense fluid flow is thermal flow sensing. Several companies including Sensirion AG, of Zurich, Switzerland, and Bronkhorst Nijverheidsstraat of Ruurlo, The Netherlands, have been developing thermal flow sensors capable of monitoring flows in nL/min ranges.

Operation of these thermal flow sensors is described with reference to FIG. 1. Heat introduced into a liquid filled tube/channel will disperse in both the upstream and downstream directions (i.e. due to thermal conduction or diffusion respectively). The tube of the flow sensing device is made from materials of low thermal conductivity (i.e. glass, plastic). A temperature profile similar to curve "A" in FIG. 1 will develop when a discrete section of the fluid in the tube is continuously heated, under a zero flow condition. The shape of this temperature profile will depend upon the amount of heat added to the fluid and the upstream and downstream temperatures of the liquid. Assuming identical upstream and downstream fluid temperatures, under a zero-flow condition, liquid temperatures measured at $P_1$ and $P_2$ will be equal as thermal diffusion will be equal in both directions.

If the liquid in the tube is permitted to flow, the fluid temperatures at $P_1$ and $P_2$ will depend upon the rate of liquid flux and the resulting heat convection. As liquid begins to flow past the heated zone, a temperature profile similar to curve B in FIG. 1 will develop. In addition to the symmetric diffusion of the heat, asymmetric convection of the heated fluid will occur in the direction of the fluid flow. Therefore, under flowing conditions, fluid temperatures measured at $P_1$ and $P_2$ will be different.

Temperature measurements made at $P_1$ and $P_2$ are sampled, subtracted and amplified electronically in situ to provide a high degree of common-mode noise rejection. This allows discrimination of extremely small upstream and downstream temperature differences. By appropriate placement of temperature measurement probes (i.e., $P_1$ and $P_2$) and/or by changing the amount of heat added to the flowing liquid, temperature measurement can be made at inflection points along the temperature profile. Measurement at the inflection points maximizes the upstream/downstream ΔT response to flow rate change.

The dynamic range of thermal flow sensing is limited by the sensitivity and precision of the temperature measurement instruments. Heat transfer via diffusion in the fluid and heat transfer to the tube walls occurs rapidly under low fluid flux conditions (i.e. <500 nL/min in tubing/channels of dimensions <100 um). Therefore, precise measurement of temperature close to the point of heat addition is required. The upper dynamic range is limited by the dynamic range of the temperature sensors and by the amount of heat that can be added to the flowing liquid.

Measuring flow in the nano-scale range with thermal flow sensors is troublesome because the thermal flow sensors are mass-sensitive. Therefore, as the flow rate decreases the size and thermal mass of the sensor must also decrease. Thermal sensors having low thermal mass are very sensitive to ambient temperature variations and drift in the incoming fluid temperature. Furthermore, thermal flow sensors must be calibrated to compensate for differences in the thermal conductivity of each liquid being measured. This a great disadvantage in liquid chromatography applications wherein fluid composition varies dramatically over the course of a chromatography run. Accordingly, presently available thermal flow sensors have inadequate precision and accuracy for use in nano-scale liquid chromatography applications heretofore known without elaborate calibration measures.

Published German Patent Application No. DE 199 14 358 A1 to Agilent Technologies, Inc. of Palo Alto, Calif. (hereinafter referred to as the "Agilent '358 publication") describes an apparatus for furnishing volumetric flow rates of liquids in capillaries, especially in chromatographic separation columns, for analytical liquid measurement, with a feed device to feed a total stream and a stream splitter to divide the total stream into an excess stream in an excess path, and an operating stream in an operating path. One embodiment of the apparatus described in the Agilent '358 publication is illustrated in FIG. 2. The apparatus 28 has at least one operating sensor 40 and a control device 85 to control the operating stream 35 and/or the pressure in the operating path 37, which is coupled to the operating sensor 40 and a means to change the operating stream 45.

The Agilent '358 publication describes volumetric measurements of flow rates for liquid chromatography as being extremely difficult and indicates that volumetric flow meters for precise measurement of extremely small flow rates of liquids with different physical properties are still unknown. To overcome this difficulty, the Agilent '358 publication describes an operating sensor designed as a volumetric flow meter. The described operating sensor records the volumetric flow rate through capillaries by using at least two detectors for detection of at least one gas bubble contained in the column stream. A time difference recording device is used to measure the travel time difference of gas bubbles through detectors.

The Agilent '358 publication also describes the possible use of mass flow sensors to record minimal volumetric flow rates of liquids in capillaries but indicates that calibration of such mass flow sensors for different solvents had previously been practically impossible. To overcome this difficulty, the Agilent '358 publication describes an elaborate calibration procedure that must be used. The elaborate calibration procedure combines volumetric flow measurement and pressure control in conjunction with means to control the operating stream.

European Patent Application No. EP 1 248 096 A1 of Agilent Technologies, Inc. of Palo Alto, Calif. (hereinafter referred to as "the Agilent '096 publication") describes an active flow-divider having a reduced back pressure sensitivity, enabling the splitting ratio to be kept constant independently of the physical properties of the fluid and/or fluctuations in pressure. The number of flow sensors used corresponds to at least the number of divided fluid streams being provided. The split ratio can then be determined according to the measurements of the at least one nano-scale flow sensor. The active splitter then can be controlled to adjust the volume of the stream branches to provide a constant volume and/or constant split ratio to at least one branch of the system. Accordingly, the method described in the Agilent '096 publication also relies on at least one nano-scale sensor in the working stream. Although the variations in splitter permeability, viscosity and/or thermal capacity of the media are theoretically compensated for, the basis of the compensation relies on nano-scale flow measurements which require elaborate calibration methods.

SUMMARY OF THE INVENTION

The present invention provides a method and apparatus for monitoring and controlling the nano-scale flow rate of fluid in the operating flow path of a HPLC system without relying on complex calibration routines to compensate for solvent composition gradients typically used in HPLC. A main flow sensor is disposed in the main flow path between the pump and a flow-divider. A second flow sensor is disposed in either the waste flow path downstream of the splitter or in the operating flow path. When the second flow sensor is disposed in the waste flow path, the output signal of the second flow sensor is subtracted from the output signal of the main flow sensor in a difference circuit to obtain an indirect measure of the flow through the operating flow path. When the second flow sensor is disposed in the operating flow path, the flow through the operating flow path is measure directly. In either case, the flow measured by the main flow sensor (i.e. the input flow to the system) is divided by the flow measured through the operating flow path (i.e. that measured indirectly by measurement of the flow through the waste flow path or that measured directly by a flow sensor in the operating flow path) in a divider circuit. The output of the divider circuit represents an empirical split ratio of the flow-divider and is independent of media composition and system permeability. The divider circuit output can optionally be fed back to a control circuit to adjust the waste stream flow rate to a desired value, for example by controlling a variable restrictor in the waste flow path or adjusting the pump flow rate to obtain a desired flow in the operating flow path. The controlled flow rates are thereby based on a measured flow ratio.

Thermal flow sensors or pressure measuring sensors as described hereinbefore can be used as upstream, waste or operating stream flow sensors with good accuracy and precision. When the flow sensor is used in the operating path, in order to obtain acceptable accuracy and precision, a sensor of different scaling from the main flow sensor is used (i.e. for a pressure-based flow sensor, a less permeable restrictor is used to produce a measurable pressure drop for nano-scale flow rates, for a thermal-based flow sensor, the sensing elements' thermal mass is scaled to allow measurement of nano-scale mass flow rates).

An illustrative embodiment of the invention includes an apparatus for measuring flow rates of a liquid in a capillary system. A main flow path carries liquid to a flow-divider. An operating flow path carries a portion of the liquid from the flow-divider according to a split ratio of the flow-divider. A waste flow path carries the remaining portion of the liquid from the flow-divider. A main flow sensor is operatively disposed with the main flow path and configured to measure volumetric flow rates of the liquid in the main flow path. A waste flow sensor is operatively disposed in the waste flow path and configured to measure volumetric flow rates of the liquid in the waste flow path. A subtractor receives a main flow signal from the main flow sensor and a waste flow signal from the waste flow sensor. The subtractor is configured to provide a difference signal representing the difference between the main flow signal and the waste flow signal. A divider receives the difference signal and the main flow signal. The divider is configured to provide a quotient signal representing the split ratio of the flow-divider.

In an illustrative embodiment, the capillary system is a high pressure liquid chromatography (HPLC) system having operating stream flow rates in the nano-scale range. The subtractor is typically implemented as an electronic subtraction circuit and the divider is typically implemented as an electronic divider circuit. The quotient signal is independent of solvent composition.

In another illustrative embodiment the main flow sensor and the waste flow sensors are thermal-type flow sensors. The thermal-type flow sensors include means for introducing heat in a flow path and means for measuring temperature (i.e., temperature sensors) of liquid in the flow path upstream and downstream of the point of introducing the heat. The thermal-type flow sensors also include means, such as a thermal flow calculator described hereinafter, for computing the volumetric flow rate of liquid in the flow path according to differences between upstream and downstream temperatures in the flow path.

In another illustrative embodiment, the main flow sensor and the waste flow sensor are pressure-type flow sensors. The pressure-type flow sensors include restrictor means disposed in a flow path and means for measuring fluid pressure upstream and downstream of the restrictor means. The pressure-type flow sensors also include means for computing the volumetric flow rate of liquid in the flow path according to the difference between pressure measured upstream of the restrictor and pressure measured downstream of the restrictor means. The means for computing volumetric flow rate of liquid can include, for example, subtractor means implemented to provide the difference (i.e., pressure drop) in pressure measured upstream and downstream of a restrictor means. Alternatively, virtually any electronic computation means can be implemented to determine liquid flow rate as a function of pressure drop across a restrictor means.

Another illustrative embodiment of the invention includes a controller that receives the quotient signal from the divider. The controller is configured to adjust the liquid flow rate in the operating flow path in response to the quotient signal. In at least one embodiment, the system includes a waste path variable restrictor operatively disposed in the waste flow path. The waste path variable restrictor is responsive to a signal from the controller to adjust the liquid flow rate in the operating flow path by varying permeability of the waste flow path. Another embodiment of the invention includes a main path pump operatively disposed in the main flow path. The main path pump 26 is responsive to a signal from the controller to adjust the liquid flow rate in the operating flow path 14 by varying output flow of the main pump.

In another illustrative embodiment, the present invention includes a method for measuring nano-scale flow rates of a liquid in a high pressure liquid chromatography (HPLC) system. The method includes measuring a main flow rate in a main flow path between a HPLC pump and a flow-divider. The flow-divider divides the main flow path into an operating flow path and a waste flow path according to a split ratio of the flow-divider. The method further includes measuring a waste flow rate in the waste flow path, subtracting the waste flow rate from the main flow rate to determine a flow rate difference and dividing the flow rate difference by the main flow rate to determine an empirical split ratio. The empirical split ratio is independent of varying liquid composition.

According to the invention, the liquid flow rate in the operating flow path can be adjusted in response to the empirical split ratio. In at least one embodiment, the liquid flow rate in the operating flow path is adjusted by changing the permeability of a variable restrictor disposed in the waste flow path. In another embodiment, the liquid flow in the operating flow path is adjusted by changing the output flow rate of the HPLC pump.

Illustrative embodiments of the present invention feature a method for measuring and controlling nano-scale flow rates in a capillary system by measuring liquid flow in the high flow rate range. In applications wherein nanoscale flow sensors are not available or are prohibitively expensive, for example, sensors that are precise, accurate and readily available are configured in the high volume stream and used to monitor and control the related nano-scale flow rate in the operating stream. A method for accurately measuring and controlling capillary fluid flows in the nL/min (nano-scale) range is provided that is not sensitive to changes in the fluid composition over time. Accordingly, the present invention is particularly useful to measure and control the operating stream to an LC (liquid chromatography) column in a HPLC system.

The present invention effectively avoids the need to calibrate thermal type sensors according to the thermal conductivity of each liquid being measured. Pressure-type thermal flow sensors may also be used within the accurate operating range of the pressure-type sensors. The present invention substantially eliminates the need to calibrate the pressure type sensors according to the viscosity of each liquid being measured or the changing permeability of the capillary system. Advantageously, the invention also minimizes the delay caused by the large internal volume of pressure-type flow sensors, by positioning the sensors in an appropriate location, such as outside of the nano-scale flow path. In applications where suitable nano scale flow sensors are not available, embodiments of the present invention provide a method and apparatus for sensing nano scale flow rates with thermal flow sensors within the accurate operating range of the thermal flow sensors.

BRIEF DESCRIPTION OF THE DRAWINGS

The foregoing and other features and advantages of the present invention will be more fully understood from the following detailed description of illustrative embodiments, taken in conjunction with the accompanying drawings in which.

DETAILED DESCRIPTION

Figure 3:
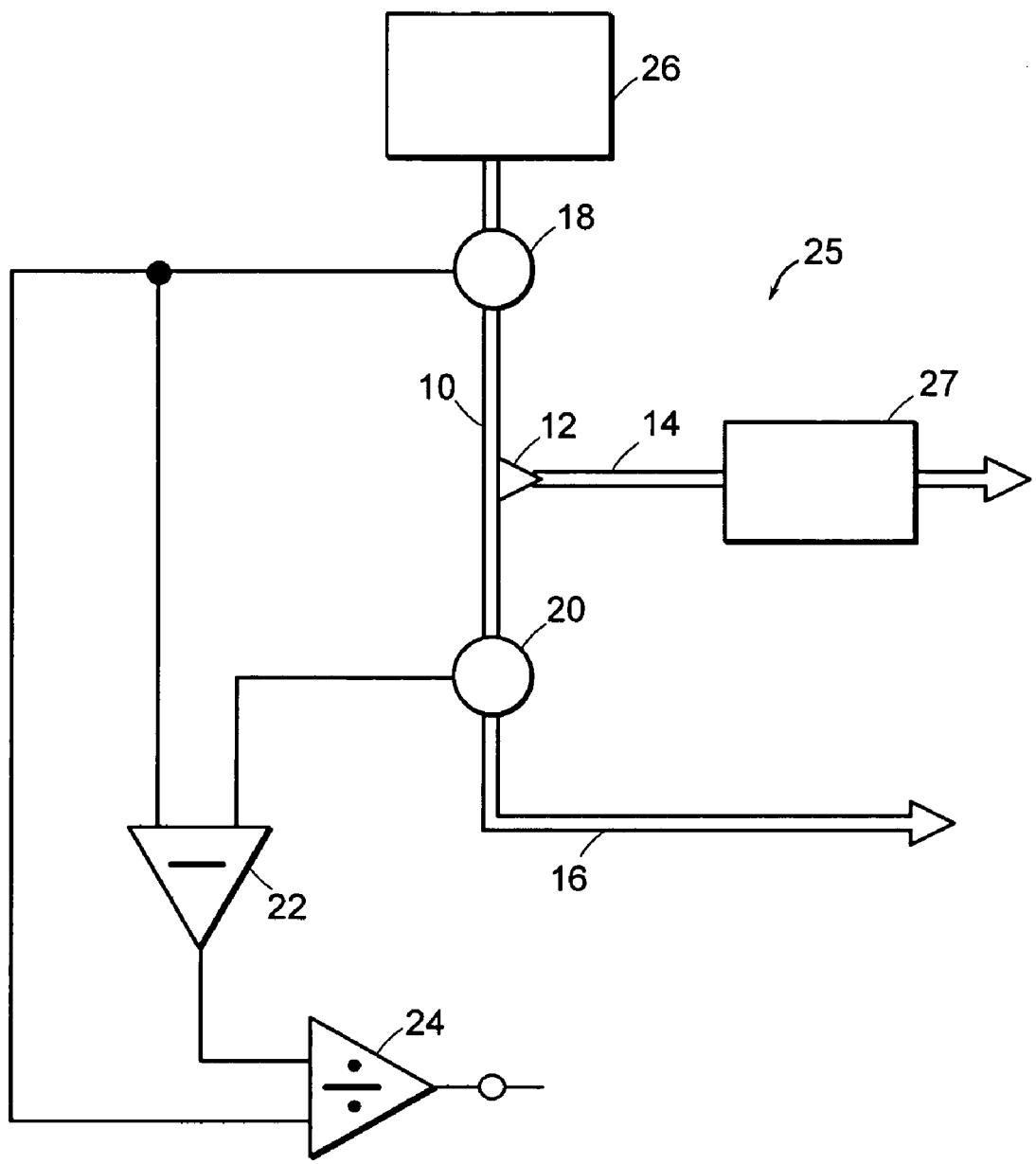
FIG. 3 is a schematic system diagram of an apparatus for measuring nano-scale flow rates of liquid in a capillary system according to an illustrative embodiment of the present invention.

An illustrative embodiment of a capillary system 25 according to the invention is described generally with reference to FIG. 3. A main flow path 10 is divided by a flow-divider 12 into an operating flow path 14 and a waste flow path 16. A main flow sensor 18 is operatively disposed in the main flow path 10. A waste flow sensor 20 is operatively disposed in the waste flow path 16. Outputs from both the main flow sensor 18 and the waste flow sensor 20 are connected to the input of a subtractor 22 for communicating volumetric flow rate signals to the subtractor 22. Outputs from both the main flow sensor 18 and the subtractor 22 are connected to inputs of a divider 24 for communicating the main volumetric flow rate signal and a difference signal to the divider 24. The output of the divider 24 can be used, for example as described hereinafter to control flow rate in an operating stream.

Figure 4:
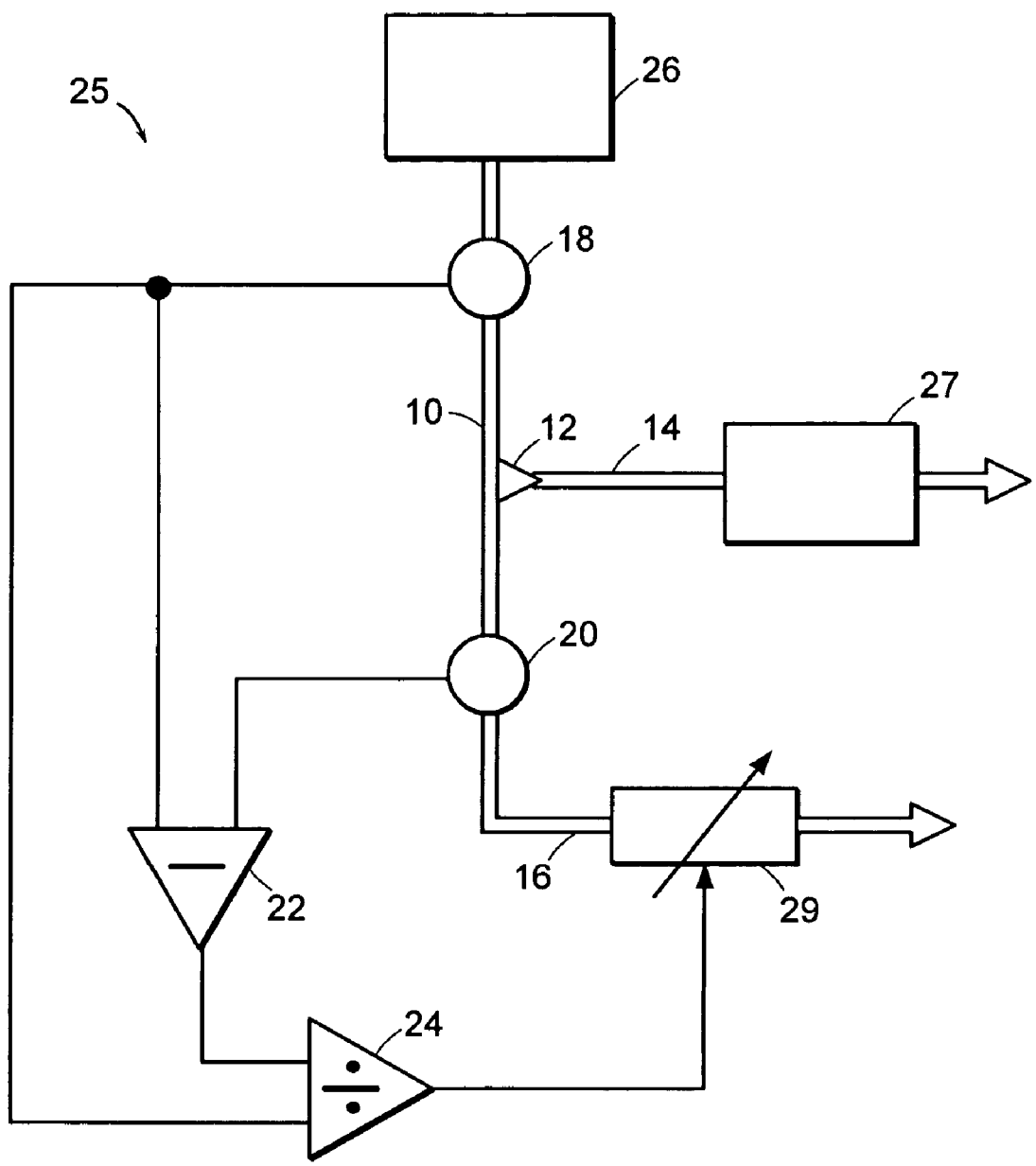
FIG. 4 is a schematic system diagram of an apparatus for measuring and controlling nano-scale flow rates in a capillary system using a variable restrictor in the waste flow path according to an illustrative embodiment of the present invention.

In an illustrative embodiment depicted in FIG. 4, the capillary system 25 is a high pressure liquid chromatography (HPLC) system. In the HPLC system, a pump 26 is operatively disposed in the main flow path 10. An HPLC column 27 is disposed in the operating flow path 14. The pump 26 is configured to provide an appropriate flow rate to the liquid (mobile phase) in the main flow path 10. The flow divider 12 and a split restrictor 29 are configured to deliver an appropriate portion of the mobile phase to the operating stream.

In an HPLC system, a normal scale HPLC pump 26 can be employed to provide a flow rate in the range of about 0.1 to 5.0 mL/min of mobile phase in the main flow path 10. A micro scale HPLC pump 26 can alternatively be employed to provide a flow rate in the range of about 1 to 100 μL/min. in the main flow path 10. The flow-divider 12 and split restrictor 29 are designed or selected to provide a split ratio appropriate to provide mobile phase to the operating flow path 14 at the desired nano-scale (nL/min.) flow rate. In alternative embodiments of the present invention the flow-divider 12 can be designed or selected to have a split ratio to provide mobile phase to the operating flow path at a desired capillary scale (1-20 μL/min) or micro-bore scale (20-100 μL/min) flow rate, for example. The flow-divider 12 includes at least one fluid restrictor (not shown) in the waste flow path 16 and/or the operating flow path 14 to achieve a desired split ratio. The resulting flow rate of mobile phase flow in the waste flow path 16 is therefore in approximately the same range as the flow rates in the main flow path 10. That is, both the main flow path 10 and waste flow path 16 carry large flow volumes compared to the nano-scale flow volumes carried by the operating flow path 14.

Any of various flow sensors capable of providing precise and accurate output signals in the micro-scale flow range can be used to implement the main flow sensor 18 and waste flow sensor 20 according to the illustrative embodiment of the invention. It is envisioned that flow sensors that provide precise and accurate output signals in the normal-scale flow range would be suitable for use as the main flow sensor 18 and/or as the waste flow sensor 20 in systems having a pump 26 configured to provide normal-scale flow in the main flow path 10. In at least one embodiment, the waste flow sensor is disposed between the flow divider 12 and split restrictor 29. This allows sensing before any delay caused by flow through the split restrictor during which solvent composition could be changing, for example.

Figure 5:
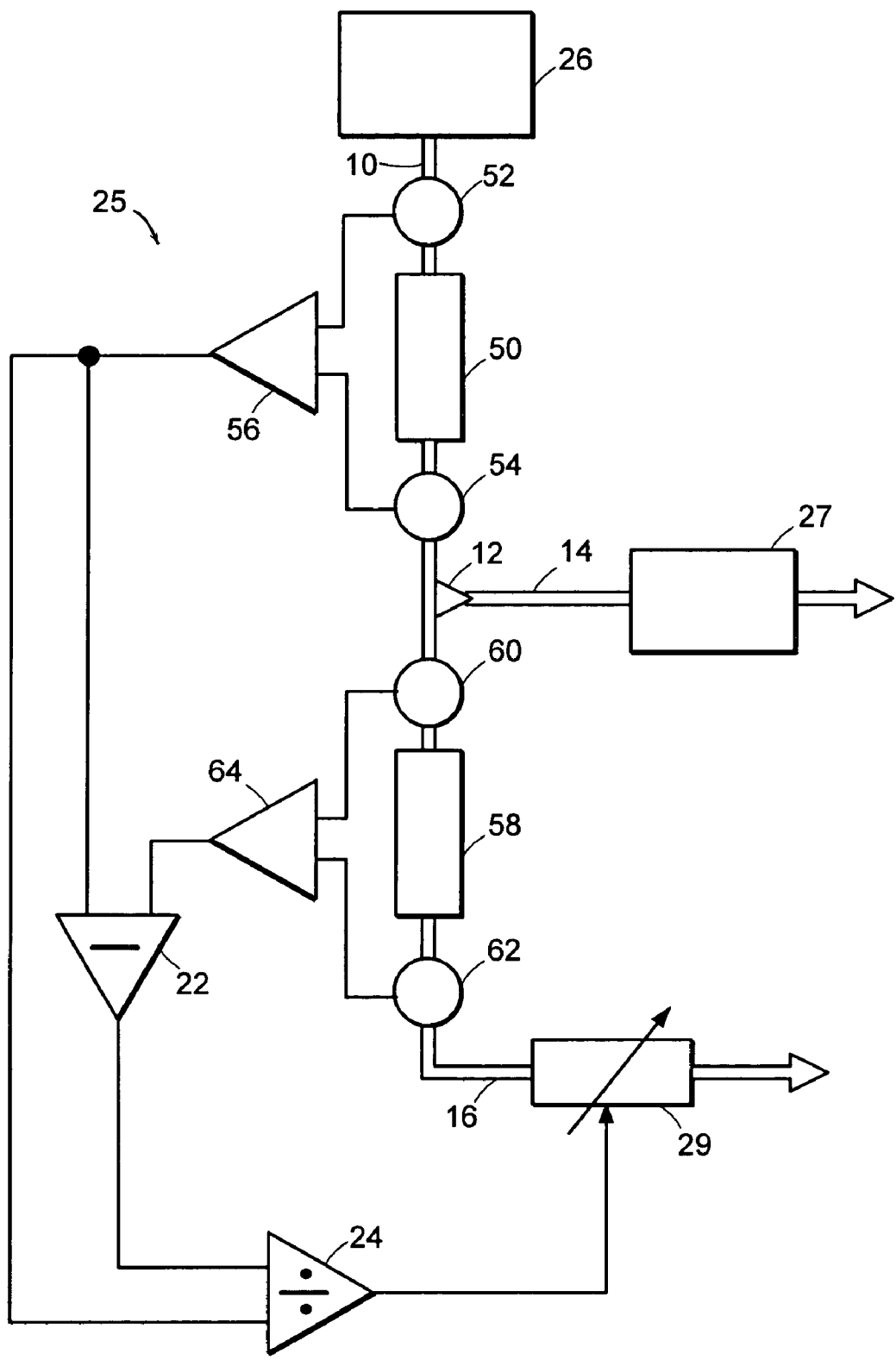
FIGS. 5 and 6 are schematic system diagrams of an apparatus for measuring and controlling nano-scale flow rates in a capillary system using pressure-type flow sensors in the main flow path and in the waste flow path according to illustrative embodiments of the present invention.
Figure 6:
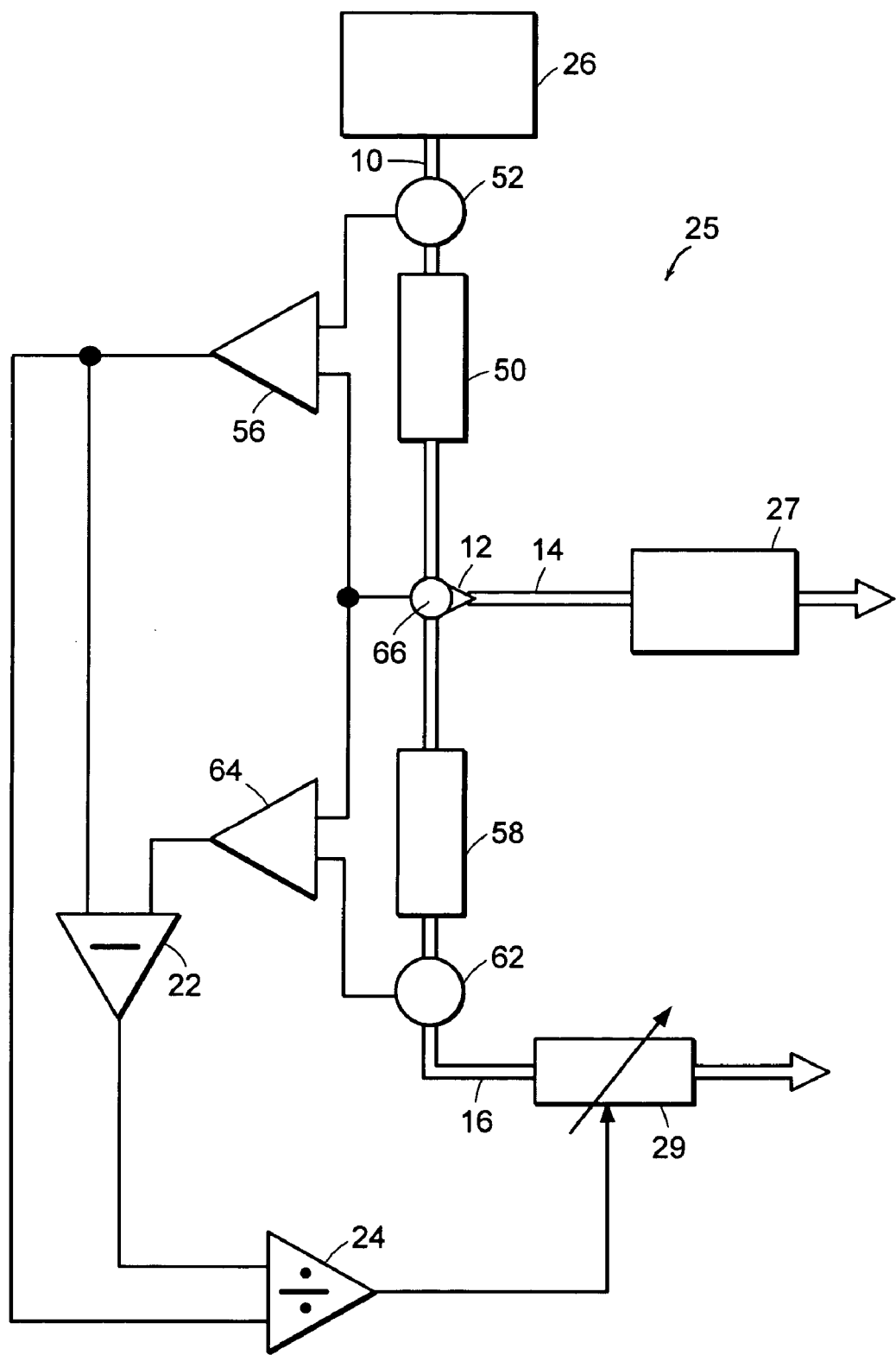
Figure 7:
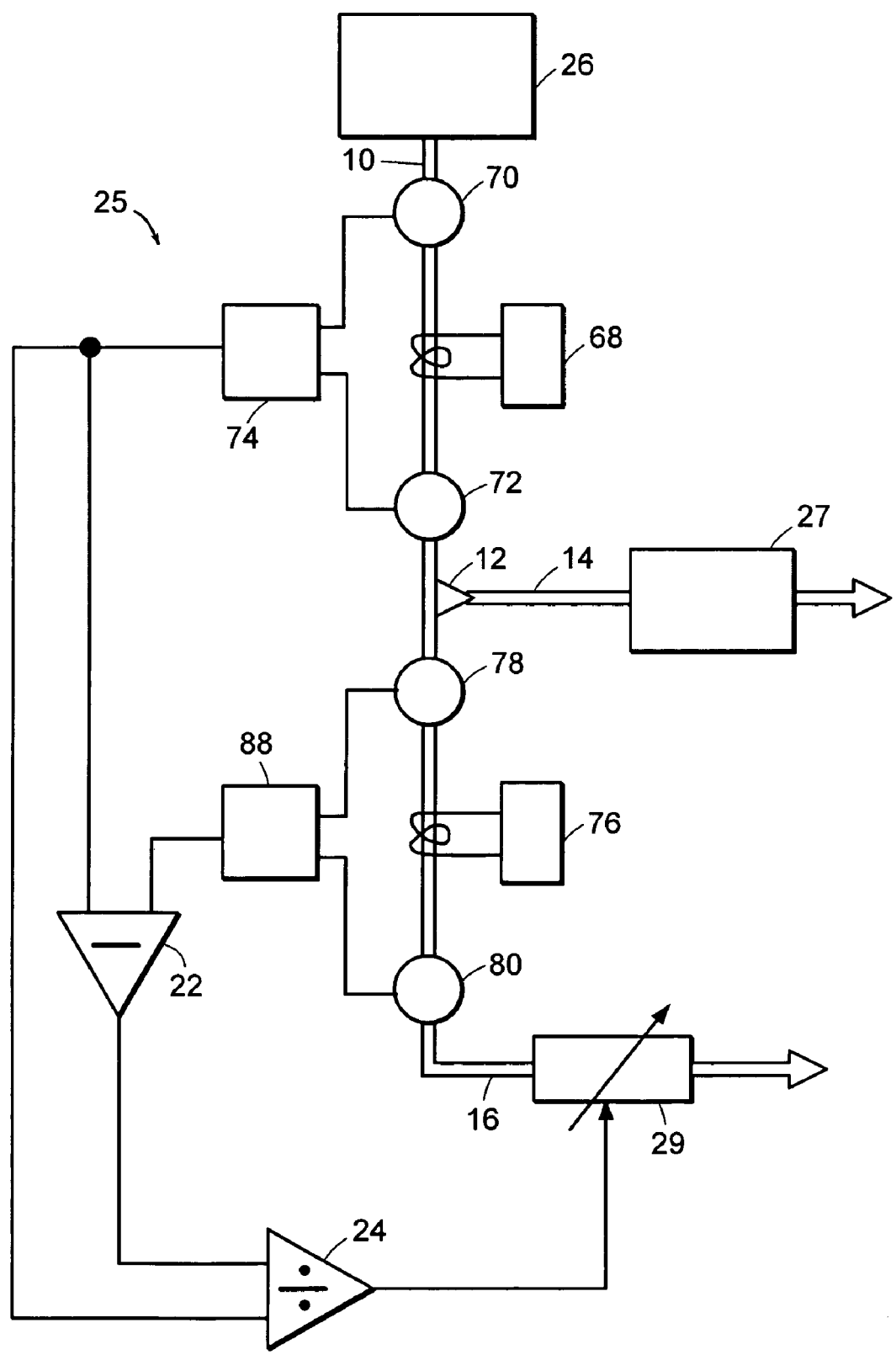
FIG. 7 is a schematic system diagram of an apparatus for measuring and controlling nano-scale flow rates in a capillary system using temperature-type flow sensors in the main flow path and in the waste flow path according to an illustrative embodiment of the present invention.

Various illustrative embodiments of flow sensors suitable for use as the main flow sensor 18 and/or the waste flow sensor 20 according to the present invention are described infra with respect to FIGS. 5-7. The measurement drift that is typically encountered at nano-scale HPLC flow rates is minimized because the flow measurements provided by the main flow sensor 18 and waste flow sensor 20 are made at relatively high mass flow rates.

The subtractor 22 is implemented as an electronic subtraction circuit as known to those skilled in the art. Input signals to the subtractor 22 represent the flow rate of mobile phase in the main flow path 10 and the flow rate of mobile phase in the waste flow path 16. The difference between these two flow rates represents the mobile phase flow rate in the operating flow path 14 and is represented in the output signal of the subtractor 22.

The divider 24 is implemented as an electronic divider 24 circuit as known to those skilled in the art. Input signals to the divider 24 represent the flow rate of the mobile phase in the main flow path 10 and the flow rate of the mobile phase in the operating flow path 14. Accordingly, the divider 24 outputs a signal representing the split ratio of the flow-divider 12. The signal output by the divider 24 according to the present invention is independent of the composition of the liquid being measured (mobile phase). Accordingly, in contrast to heretofore known systems for measuring flow rates in a range from about 10 nL/min. to about 1000 mL/min. which must typically be calibrated for particular liquid composition, the flow sensing method of the present invention is insensitive to the composition of the fluid being measured.

In an illustrative embodiment of the invention, output from the divider 24 is used to control the flow rate in the operating stream. FIG. 4 illustrates an embodiment of the invention wherein the flow rate in the operating stream is controlled by adjusting a the permeability of a waste path variable resistor, in the form of a variable restrictor 29 disposed in the waste flow path 16 and operatively connected to the output of the divider 24. Persons having ordinary skill in the art should appreciate that additional control circuitry (not shown) may be required between the output of the divider 24 and the input of the variable restrictor. For example, additional control circuitry may be implemented to condition the divider 24 output signal for use as an appropriate control input to the particular variable restrictor being used. Circuit components such as buffers, inverters, amplifiers and/or microcontrollers, for example, can be used to implement the control circuitry according to a number of methods that are well known to those skilled in the art.

In illustrative embodiments of the invention, a microcontroller or microprocessor (not shown) is implemented between the divider 24 output and the control input of the variable restrictor. The microcontroller or microprocessor can be programmed and configured, for example, to adjust the permeability of the variable restrictor and/or the flow rate of the pump 26 to a setting appropriate for maintaining a constant flow rate in the operating flow path 14.

An illustrative embodiment of a capillary system 25 according to the present invention using pressure-type flow sensors is diagrammed in FIG. 5. A restrictor means 50, 58 is disposed in both the main flow path 10 and the waste flow path 16. Restrictor means can include virtually any structure or method for impeding the flow of fluid in a flow path in a predictable manner to create a predictable pressure drop from one side of the restrictor means to the other. For example, a length of capillary tubing having a precisely dimensioned inside diameter can be a suitable restrictor means in some embodiments of the invention. It is envisioned that screens, filters and other impediments to flow could also be disposed in the flow path for use as restrictor means in various embodiments of the invention. Certain other embodiments of the invention require variable restrictor means wherein the impediment to fluid flow can be controlled as known in the art.

Pressure sensing means 52, 54, 60, 62 are operatively disposed upstream and downstream of each restrictor means 50, 58 in their respective flow path. Pressure sensing means suitable for the use in the present invention can include pressure transducers that are commonly available. Pressure sensing means should have an operating range and precision suitable to accurately detect the pressure drop across a particular restrictor. Pressure sensing means 52, 54, 60, 62 may include virtually any type of pressure sensor providing an electronic output signal and having sufficient accuracy and precision to measure pressure within the dynamic range of the fluid system.

Typical pressure sensing means generate analog voltage signals having a magnitude proportional to the pressure being sensed. It is envisioned that virtually any type of output from an appropriate pressure sensing means could be used in the present invention. For example, it is envisioned that various pressure sensing means could generate a pressure dependent electric current, a pressure dependent modulated signal, a pressure dependent variable resistance, a variable capacitance, an optical signal and the like. Accordingly, certain pressure sensing means also incorporate various other components, for example, as signal conditioning components, to amplify an output signal or convert the signal to a form more suitable for use in a particular system.

The outputs of the upstream and downstream pressure sensing means 52, 54 in the main flow path 10 are connected to main flow path 10 pressure subtractor means 56. Subtractor means include virtually any electronic subtraction circuitry as known in the art. Suitable subtractor means can include, for example, a standard operational amplifier (op-amp) subtraction circuit. Alternatively, an analog to digital (A/D) converter can be implemented to convert a signal to digital form so digital subtractor means such as a microcontroller, or personal computer can be used as subtractor means as known in the art. The outputs of the upstream and downstream pressure sensing means 60, 62 in the waste flow path 16 are connected to waste flow path 16 pressure subtractor means 64. Outputs from the main stream pressure subtractor means 56 and waste stream pressure subtractor means 64 correspond to output of the main flow sensor 18 and waste flow sensor 20, respectively (see FIGS. 3 and 4), and are connected to the input of the subtractor 22. The inputs to the subtractor 22 correspond to the flow rates in the main flow path 10 and the waste flow path 16 because the flow through each restrictor is linearly related to the pressure drop across it.

Another embodiment of a capillary system 25 according to the present invention using pressure-type flow sensors is diagrammed in FIG. 6. A restrictor means 52, 58 is disposed in both the main flow path 10 and the waste flow path 16. Pressure sensing means are operatively disposed upstream and downstream of each restrictor means in their respective flow path. However, in the embodiment depicted in FIG. 6, a single flow-divider pressure sensing means 66 serves to measure fluid pressure down stream of restrictor 50 in the main flow path 10 and upstream of the restrictor 58 in the waste flow path 16. The system illustrated in FIG. 6 is substantially similar to the system illustrated in FIG. 5 except that a single pressure sensing means is used to provide a measurement of liquid pressure on the downstream side of the main flow restrictor and on the upstream side of the waste stream restrictor. The single pressure sensing means is incorporated with the flow-divider 12.

The outputs of the upstream pressure sensing means 52 and flow-divider pressure sensing means 66 in the main flow path 10 are connected to main flow path 10 pressure subtractor means 56. The outputs of the flow-divider pressure sensing means 66 and downstream pressure sensing means 62 in the waste flow path 16 are connected to waste flow path pressure subtractor means 64. Outputs from the main stream pressure subtractor 22 means and waste stream pressure subtractor 22 means correspond to output of the main flow sensor 18 and waste flow sensor 20, respectively (see FIGS. 3 and 4), and are connected to the input of the subtractor 22. The inputs to the subtractor 22 correspond to the flow rates in the main flow path 10 and the waste flow path 16 because the flow through each restrictor is linearly related to the pressure drop across it.

FIG. 7 illustrates an embodiment of the invention which uses thermal-type flow sensors. In the illustrative embodiment depicted in FIG. 7, a means for introducing heat, i.e., a main path heater 68 is disposed at a discrete location to inject heat into the fluid flowing in the main flow path. The means for introducing heat can include any structure or method for heating a discrete segment of the fluid stream. For example, it is envisioned that an electric heater coil connected to an accurate temperature controller can be wrapped around a small segment of the flow path.

Figure 1:
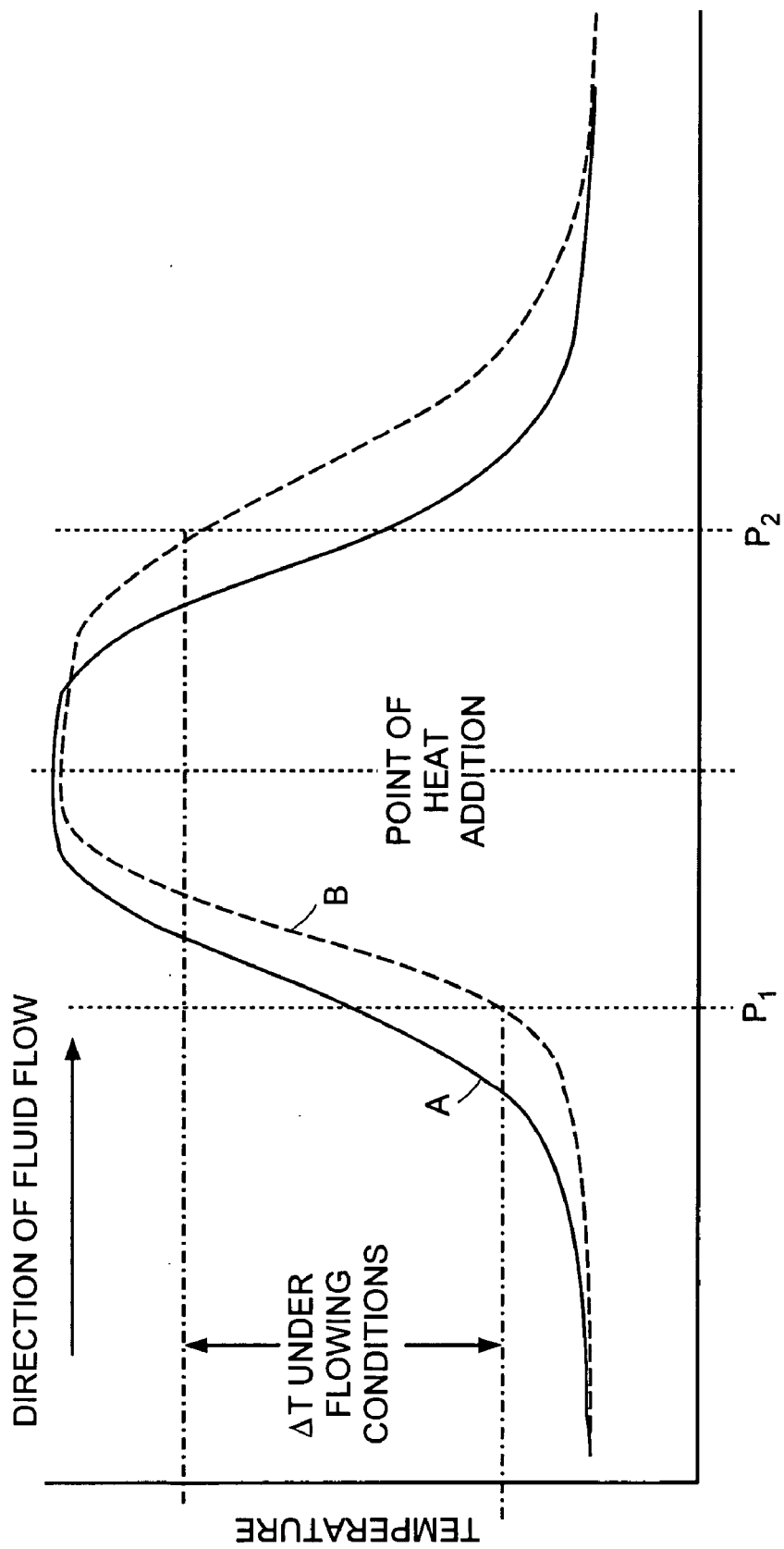
FIG. 1 is a graphical representation of the temperature distance between sensors used in thermal-type flow sensing according to the PRIOR ART.

Main path temperature sensors 70, 72 are placed upstream and downstream of the main path heater 68. Outputs from the main path temperature sensors 70, 72 are communicated to a main path thermal flow calculator 74. A waste path heater 76 is disposed at a discrete location to inject heat, i.e., a heat plug, into the fluid flowing in the waste flow path 16. Waste path temperature sensors 78, 80 are placed upstream and downstream of the waste path heater 76. Outputs from the waste path temperature sensors 78, 80 are communicated to a waste path thermal flow calculator 88. The main path thermal flow calculator 74 and waste path thermal flow calculator 88 are components of the thermal flow sensors described hereinbefore with respect to FIG. 1 which each compute the flow rates in their corresponding flow paths according to means well known in the art. Each thermal flow calculator 74, 88 outputs a signal representing the flow rate in its corresponding flow path.

A number of electronic circuits known in the art can serve as thermal flow calculators 74, 88 according to the present embodiment. For example, microprocessor circuits, microcontrollers, ASICs (application specific integrated circuits), or analog comparison circuitry are all well known in the art and can be configured to compare outputs from the temperature sensors 70, 72, 78 and 80 and calculate fluid flow rates in their respective flow path. Alternatively, thermal flow calculators 74, 88 can be implemented in software in a personal computer having a data acquisition port for accepting outputs for the temperature sensors 70, 72, 78 and 80.

The output signals from the thermal flow calculators 74, 88 are communicated as flow signals to the subtractor 22 and divider 24 as described hereinbefore with respect to outputs from the main flow sensor 18 and the waste flow sensor 20.

In an alternative embodiment, (not shown) tubes carrying mobile phase flow from the pump 26 and to the flow-divider 12 are disposed adjacent to each other. A common heater is used to heat the flows through both paths. Temperature sensors are disposed downstream in each tube at substantially identical distances from the heater. Because a common heater is used, the tubing and temperature sensors are placed in close proximity and the difference between the thermal signals is calculated electronically, a high degree of common-mode noise rejection is achieved. Such effective noise rejection allows measurements of minute differences between the flow rate in the main flow path 10 and the flow rate in the waste flow path 16.

Although the embodiments of the invention that are depicted in FIGS. 4-7 use a variable restrictor 29 in the waste flow path 16, the flow in the operating flow path 14 could also be controlled by varying the flow controls of the pump 26.

Figure 8:
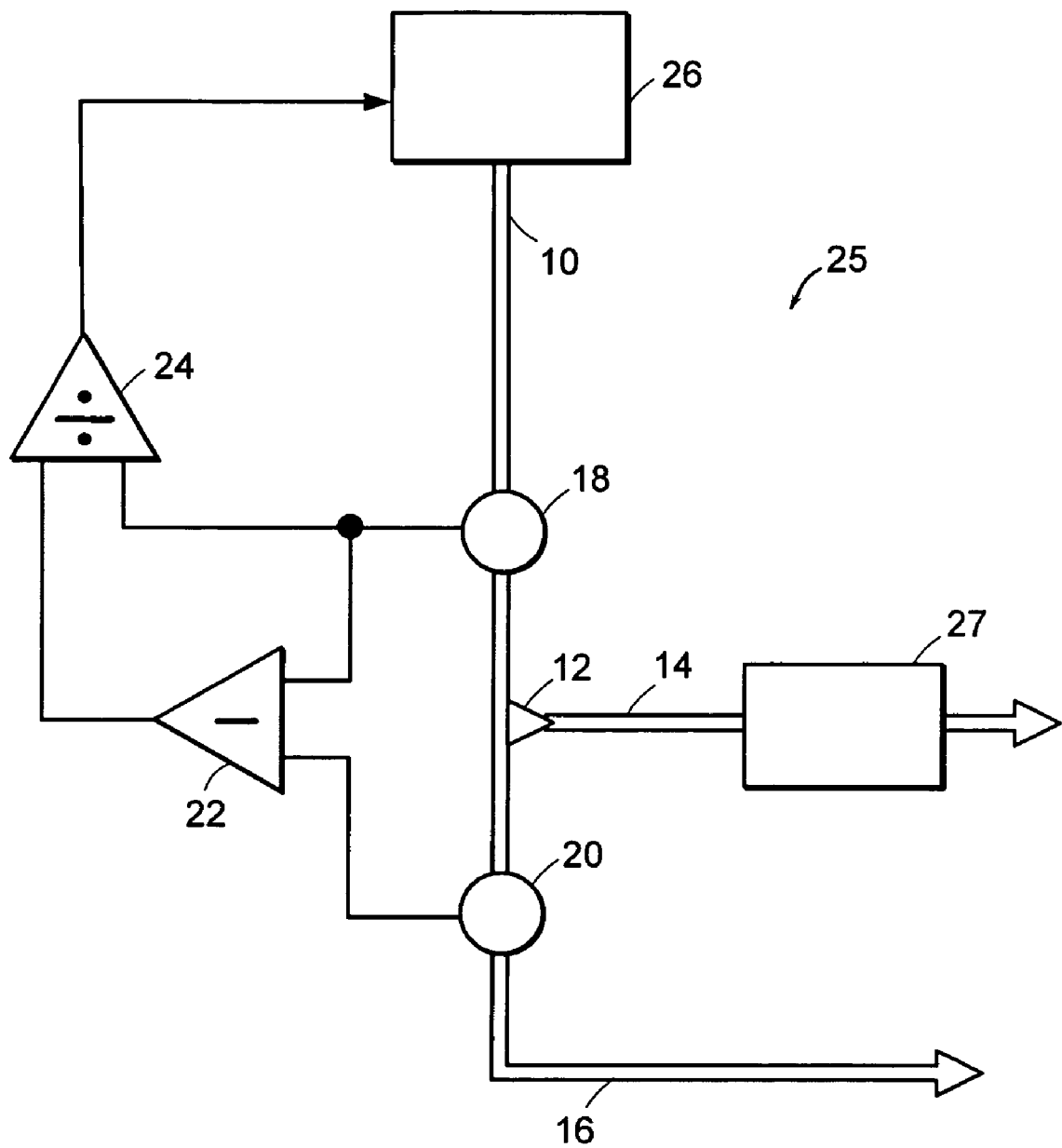
FIG. 8 is a schematic system diagram of an apparatus for measuring and controlling nano-scale flow rates in a capillary system using feedback signals to control the system pump according to an illustrative embodiment of the present invention.

In another embodiment of the invention, the flow rate in the operating stream can be controlled by directly adjusting the pump output to the main stream rather than by adjusting any variable restrictor. For example, FIG. 8 illustrates an embodiment of the invention wherein the flow rate in the operating stream is controlled by adjusting pump 26 settings in response to variations in the measured flow. In FIG. 8, (as in the embodiments described in FIG. 3) a main flow path 10 is divided by a flow-divider 12 into an operating flow path 14 and a waste flow path 16. A main flow sensor 18 is operatively disposed in the main flow path 10. A waste flow sensor 20 is operatively disposed in the waste flow path 16. Outputs from both the main flow sensor 18 and the waste flow sensor 20 are connected to the input of a subtractor 22 for communicating volumetric flow rate signals to the subtractor 22. Outputs from both the main flow sensor 18 and the subtractor 22 are connected to inputs of a divider 24 for communicating the main volumetric flow rate signal and a difference signal to the divider 24. The output from the divider 24 is operatively connected to the pump 26 for adjusting the pump settings.

Persons skilled in the art should appreciate that additional control circuitry (not shown) may be required between the output of the divider 24 and the control input of the pump 26. For example, additional control circuitry may be implemented to condition the divider output signal (quotient signal) for use as an appropriate control input to the particular pump 26 being used. Circuit component such as buffers, inverters, amplifiers and/or microcontrollers, for example, can be used to implement the control circuitry according to a number of methods that are well known in the art. Alternatively, the pump 26 may be controlled by a personal computer or workstation (not shown) having input/output circuitry connected to the pump 26 and divider 24 and having software which adjusts the pump setting in response to the quotient signal output from the divider 24.

Figure 2:
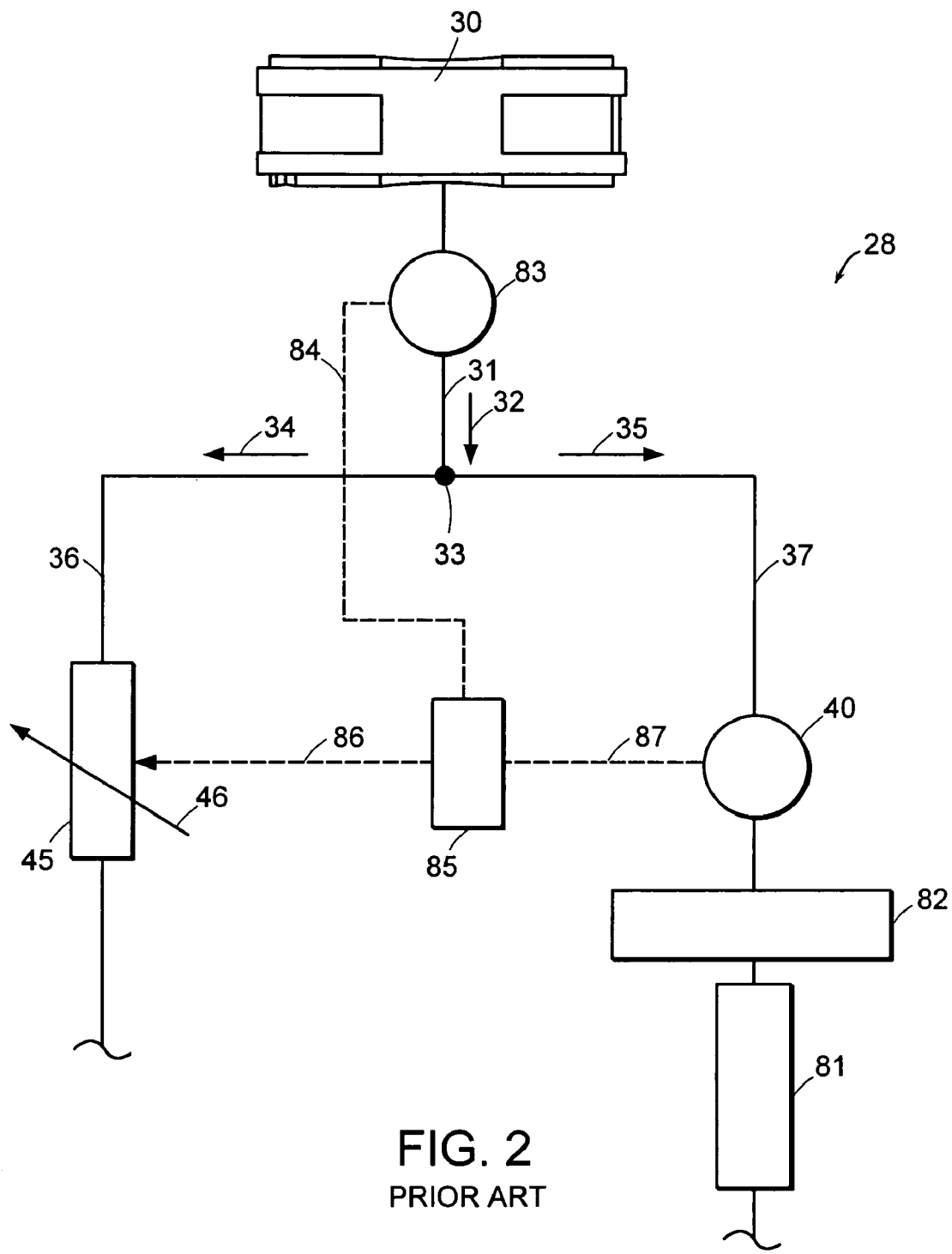
FIG. 2 is a schematic system diagram of an apparatus for measuring volumetric flow rates of liquids in capillaries according to the PRIOR ART.

Although embodiments of the present invention are described hereinbefore as having a first flow detector in the main flow path and a second flow detector in the waste flow path, an additional embodiment of the present invention is implemented by disposing the second flow detector in the operating flow path rather than the waste flow path. This additional embodiment provides advantages over the prior art described hereinbefore with respect to FIG. 2 because, unlike the prior art, the outputs from the two flow detectors are used to produce a quotient signal that represents the split ratio which is independent of the varying liquid composition.

Figure 9:
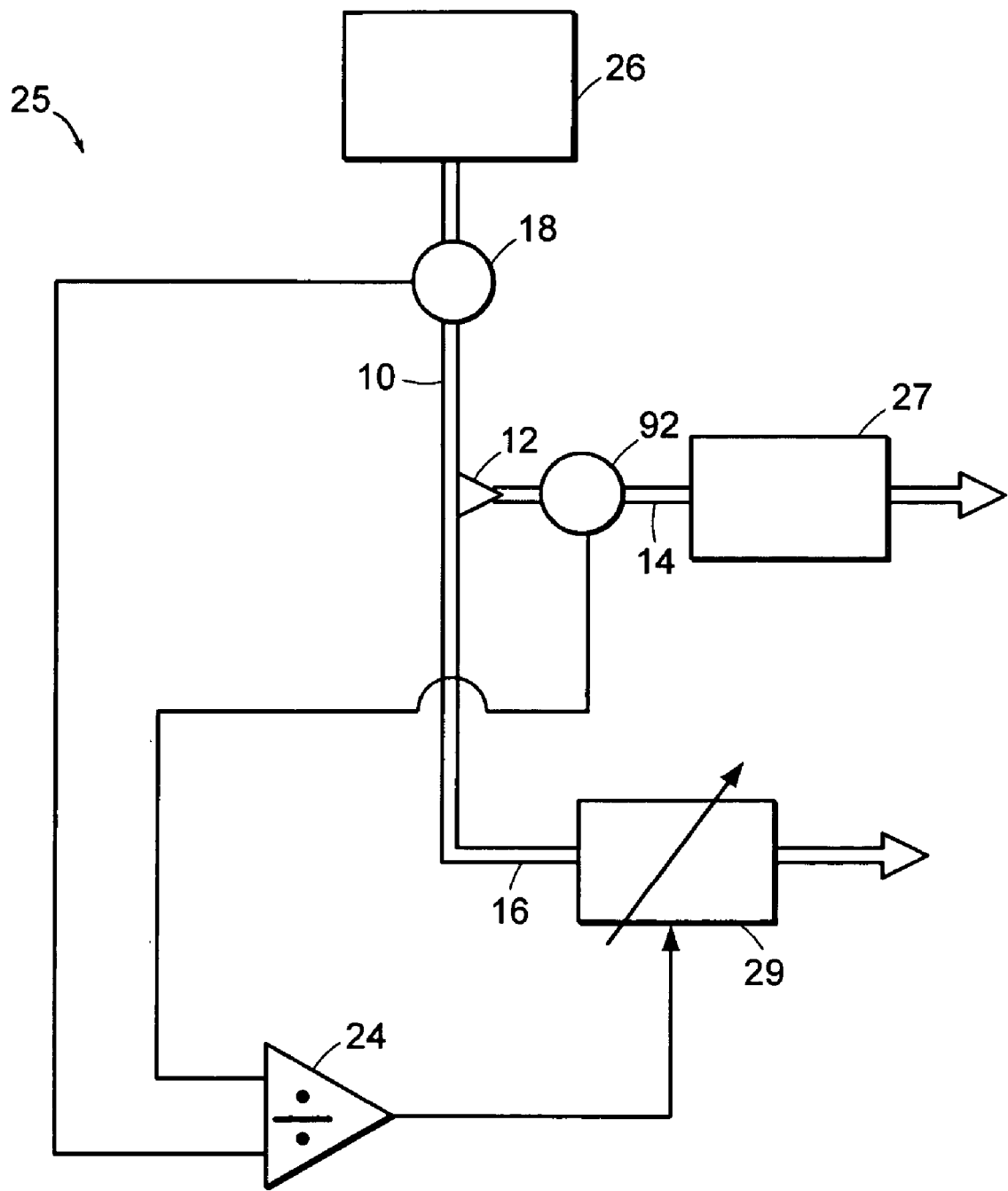
FIG. 9 is a schematic diagram of an apparatus for measuring and controlling nano-scale flow rates in a capillary system using feedback signals from a sensor in the operating flow path according to an alternative embodiment of the present invention.

The additional embodiment is described with reference to FIG. 9 in which a main flow path 10 is divided by a flow-divider 12 into an operating flow path 14 and a waste flow path 16. A main flow sensor 18 is operatively disposed in the main flow path 10. An operating flow sensor 92 is operatively disposed in the operating flow path 14. Outputs from both the main flow sensor 18 and the operating flow sensor 20 are connected to inputs of a divider 24 for communicating the main volumetric flow rate signal and operating stream flow rate signal to the divider 24. The output of the divider 24 can be used, for example as described hereinafter to control flow rate in an operating stream. The flow rate in the operating stream can be controlled, for example, by adjusting a the permeability of a waste path variable resistor, in the form of a variable restrictor 29 disposed in the waste flow path 16 and operatively connected to the output of the divider 24 and/or by adjusting the flow rate controls of the pump 26.

Although flow sensors are described herein in terms of specific thermal type flow sensors and pressure-type flow sensors, persons skilled in the art should appreciate that any number of various flow sensor types may be substituted therefor without departing from the spirit and scope of the present invention. For example several types of commercially available sensors can be used as main stream flow sensors and/or waste stream flow sensors according to the present invention.

Although various embodiments of the present invention are described herein in terms of separate circuit components for comparing pressure or temperature from various sensor components, persons skilled in the art should appreciate that a single circuit component can be implemented to serve multiple comparison functions according to the present invention. For example, a single microcontroller having multiple measurement input ports and control output ports can be used to receive and process upstream and downstream temperature and/or pressure signals to compute main path waste path flow rates and generate output signals for communicating to the subtractor and divider. An application specific integrated circuit (ASIC) could also be designed, for example, to perform these functions as well as incorporating the functions of the subtractor and divider, either by digital or analog operation, without departing from the spirit and scope of the present invention.

Although embodiments of the present invention are described herein which control flow rates in the operating stream indirectly by controlling a variable restrictor in the waste flow path or the main flow path, or by controlling the pump or variable split vent, persons skilled in the art should appreciate that these various control elements could be also implemented in various combinations according to the present invention.

Although the various embodiments of the present invention are described for use in measuring nano-scale flow rates in an HPLC system, persons skilled in the art should appreciate that the present invention can be used to measure and control a variety of different capillary systems, or fluid control and analysis systems without departing from the spirit and scope of the invention.

Although the invention is described hereinbefore with respect to illustrative embodiments thereof, persons having ordinary skill in the art should appreciate that the foregoing and various other changes, omissions and additions in the form and detail thereof may be made without departing from the spirit and scope of the invention.

What is claimed is:

1. A method for measuring nano-scale flow rates of a liquid in a high pressure liquid chromatography (HPLC) system comprising:
    measuring a main flow rate in a main flow path between an HPLC pump and a flow-divider;
    dividing said main flow path into an operating flow path and a waste flow path according to a split ratio of said flow-divider;
    measuring a waste flow rate in said waste flow path;
    subtracting said waste flow rate from said main flow rate to determine a flow rate difference;

dividing said flow rate difference by said main flow rate to determine an empirical split ratio.

2. The method according to claim 1 wherein said empirical split ratio is independent of varying liquid composition.

3. The method according to claim 1 further comprising: adjusting the liquid flow rate in said operating flow path in response to said empirical split ratio.

4. The method according to claim 3 further comprising disposing a variable restrictor in said waste flow path and wherein said liquid flow rate in said operating flow path is adjusted by changing the permeability of said variable restrictor.

5. The method according to claim 3 wherein said step of adjusting involves adjusting liquid flow in said operating flow path by changing the output flow rate of said HPLC pump.

* * * * *